_United States Patent_ [19]

Fischer et al.

[11] Patent Number: 5,679,863
[45] Date of Patent: Oct. 21, 1997

[54] PREPARATION OF CARBONYLPHOSPHINE OXIDES

[75] Inventors: Martin Fischer, Ludwigshafen; Eckhard Hickmann, Dannstadt-Schauernheim; Rudolf Kropp; Jochen Schroeder, both of Limburgerhof; Beate Trentmann, Mannheim, all of Germany

[73] Assignee: BASF Aktiengesellschaft, Ludwigshafen, Germany

[21] Appl. No.: 543,319

[22] Filed: Oct. 16, 1995

Related U.S. Application Data

[62] Division of Ser. No. 116,955, Sep. 7, 1993, Pat. No. 5,504,236.

[30] Foreign Application Priority Data

Sep. 12, 1992 [DE] Germany .............. 42 30 555.1

[51] Int. Cl.⁶ .................................. C07F 9/40

[52] U.S. Cl. ............... 568/17; 568/8; 564/15; 558/168; 558/192; 558/193; 558/207; 558/214

[58] Field of Search ................ 564/15; 558/168, 558/207, 192, 193, 214; 568/17

[56] References Cited

U.S. PATENT DOCUMENTS

| 3,351,681 | 11/1967 | Deinet .................. 260/953 |
| 3,467,622 | 9/1969 | Weil et al. ............. 260/45.95 |
| 3,515,537 | 6/1970 | Weil et al. ............. 71/86 |

_Primary Examiner_—Marianne M. Cintins
_Assistant Examiner_—Dwayne C. Jones
_Attorney, Agent, or Firm_—Keil & Weinkauf

[57] ABSTRACT

The preparation of α-carbonylphosphine oxides by oxidizing an α-hydroxyalkyl phosphine oxide with an organic hydroperoxide or of an organic peroxy acid in the presence of a compound of a Group IV to Group VIII metal in the periodic table, and novel α-hydroxybenzyl phosphine oxides. α-Carbonylphosphine oxides are used as photoinitiators for polymerizable compositions.

3 Claims, No Drawings

PREPARATION OF CARBONYLPHOSPHINE OXIDES

This is a Division of application Ser. No. 08/116,955, filed Sep. 7, 1993, now U.S. Pat. No. 5,504,236.

The present invention relates to novel methods of preparing α-carbonylphosphine oxides and to novel α-hydroxyalkyl phosphine oxides.

α-Carbonylphosphine oxides are used as photoinitiators in polymerizable compositions.

EP-A 007,508 describes a process for the preparation of α-carbonylphosphine oxides by the reaction of carboxylic chlorides with alkoxyphosphines. Stoichiometric amounts of alkyl chlorides are formed as undesirable by-products in these reactions. Furthermore, some acid chlorides are obtainable only with difficulty. Thus, for example, o,o-disubstituted benzoic acids can be prepared by complicated means only, ie, by haloform reaction of the corresponding acetophenones (EP-A 046,194). However, these benzoic acids are particularly desirable starting materials for industrially highly significant photoinitiators.

The reaction of disubstituted phosphine oxides with aldehydes and ketones in the presence of bases to form α-hydroxyalkyl phosphine oxides is described in *J. Am. Chem. Soc.*, 79, 424 (1957). Inter alia, compounds which are phenyl-substituted on the α-carbon atom are prepared by this method.

The preparation of some para-substituted α-hydroxybenzyldiphenyl phosphine oxides from diphenyl chlorophosphine, an aqueous mineral acid, and an aromatic aldehyde is described in *J. Org. Chem.*, 34, 748 (1969), in which the para-substituents include methyl, methoxy, chlorine, and the nitro group.

There has also been disclosed a method of using tert-butylhydroperoxide as a selective oxidizing agent for aliphatic and cycloaliphatic secondary alcohols in the presence of vanadyl acetylacetonate, as disclosed in *Tetrahedron Lett.* 24, 5009 (1983).

It is an object of the invention to find a novel process which produces α-carbonylphosphine oxides using readily obtainable compounds as starting point. Another object is to provide a process which makes it possible to prepare the particularly interesting primary stages, namely α-hydroxyphosphine oxides carrying a 2,6-disubstituted phenyl radical on the α-carbon atom and to convert said products to α-carbonylphosphine oxides. Accordingly we have found a process for the preparation of α-carbonylphosphine oxides, wherein an α-hydroxyalkyl phosphine oxide is oxidized with an organic hydroperoxide or an organic peroxy acid in the presence of a compound of a Group IV to Group VIII metal in the periodic table.

In addition, we have found a process for the preparation of α-carbonylphosphine oxides, wherein a) a disubstituted phosphine oxide is caused to react with an aldehyde to form an α-hydroxyalkyl phosphine oxide and b) this reaction product is oxidized with an organic hydroperoxide or an organic peroxy acid in the presence of a compound of a Group IV to Group VIII metal in the periodic table.

We have also found novel α-hydroxybenzyl phosphine oxides.

The first-named process converts α-hydroxyalkyl phosphine oxides to α-carbonylphosphine oxides. This reaction can be represented by the following diagram:

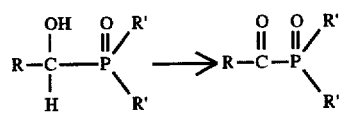

As far as we have observed, the nature of the substituents R and R' has no appreciable influence on the outcome of the process.

Some of the starting materials are known in the art, or they can be prepared by known techniques (Houben-Weyl, *Methoden der organischen Chemie*, Vol. 12/1, pp. 154, 260, 475 (1963)).

With a view to the end products which are mainly desired, those compounds are preferred which carry the following substituents on the phosphorus atom:

$C_1$–$C_{10}$ alkyl, such as methyl, ethyl, isopropyl, butyl, hexyl and preferably $C_6$–$C_8$ alkyl, especially n-octyl;

$C_3$–$C_8$ cycloalkyl and preferably cyclopentyl and cyclohexyl;

benzyl;

$C_6$–$C_{10}$ aryl and preferably phenyl, where the phenyl radical can be substituted, preferably by chlorine, dichlorine, methyl, ethyl, isopropyl, tert-butyl, dimethyl, methoxy, ethoxy, dimethoxy;

$C_1$–$C_6$ alkoxy such as methoxy, ethoxy, isopropoxy, butoxy and preferably ethoxy;

aryloxy, such as phenoxy or methylphenoxy;

ethyloxyethoxy;

benzyloxy;

S- or N-containing five-membered or six-membered rings such as thienyl or pyridyl.

The substituents can be the same or different.

Diphenyl phosphine oxide, phenylethoxy phosphine oxide and diethoxy phosphine oxide are particularly preferred.

The preferred compounds carry the following substituents on the α-carbon atom:

$C_1$–$C_{18}$ alkyl such as ethyl, isopropyl, n-propyl, n-butyl, tert-butyl, isoamyl, n-hexyl, n-heptyl, n-octyl, 2-ethylhexyl, isononyl, dimethylheptyl, lauryl, stearyl;

$C_3$–$C_8$ cycloalkyl and preferably $C_5$–$C_7$ cycloalkyl such as cyclopentyl, cyclohexyl, methylcyclohexyl;

$C_6$–$C_{12}$ aryl such as naphthyl but preferably phenyl, and the phenyl ring can carry one or more substituents such as halogen, eg, chlorine and bromine, alkyl such as methyl, ethyl, isopropyl, tert-butyl, alkoxy such as methoxy and isopropoxy, hydroxy, nitro, dimethylamino, more preferably 2,6-disubstituted phenyl such as 2,6-dimethylphenyl, 2,6-dichlorophenyl, and 2,4,6-trimethylphenyl;

hetero aryl such as furfuryl.

The α-hydroxyalkyl phosphine oxides are caused to react with organic peroxy acids or organic hydroperoxides. Suitable organic peroxy acids are, eg, peracetic acid, perbenzoic acid and o-chloroperbenzoic acid. But organic hydroperoxides are preferred.

Preferred suitable compounds are tert-butylhydroperoxide and cumene hydroperoxide. All hydroperoxides used can be used in commercial, ie, hydrous form or in anhydrous form, diluted with an inert solvent such as tert-butanol, toluene, or cumene. As a rule, for each mole of α-hydroxyalkyl phosphine oxide there are used from 1 to 3 mol and preferably from 1 to 1.6 mol of hydroperoxide.

Suitable catalysts for the reaction are compounds of the transition metals in Groups IV to VIII. The IUPAC nomenclature is used as basis here. The groups include the titanium, vanadium, chromium, manganese, and iron groups. Of the metal compounds, those of vanadium, molybdenum, and tungsten are preferred. More specifically, vanadium pentoxide, vanadyl(IV) bis(diphenyl phosphinate) can be used and more especially vanadyl(IV) bis-acetylacetonate. Generally speaking, the amount of catalyst used is from 0.1 to 10 mol % and preferably from 0.5 to 5 mol %, based on the α-hydroxyalkyl phosphine oxide.

The reaction is advantageously carried out in an inert solvent. Suitable examples thereof are tert-butanol, acetic acid, acetonitrile, methylene chloride, methyl-tert-butyl ether, benzene, toluene, and chlorobenzene. Generally speaking, the amount of solvent is from 50 to 90 wt % of the total batch.

All components can be mixed or, in a preferred embodiment, the hydroperoxide—if desired with cooling to from 0° to 10° C.—is added to the other components. The temperature is not normally increased to more than 100° C., since room temperature is usually sufficient to complete the reaction in a few hours. Since the pressure has no discernible influence on the reaction, it is carried out usually under standard pressure conditions.

The isolation of the products is carried out by known techniques, for example by distillation or crystallisation.

Since the α-hydroxyalkyl phosphine oxides are not commercially available, they must also be prepared, and, starting from the aldehydes, the following two-stage overall process for the preparation of the α-carbonylphosphine oxides results, wherein a) a disubstituted phosphine oxide is caused to react with an aldehyde to form an α-hydroxyalkyl phosphine oxide and b) this reaction product is oxidized with an organic hydroperoxide or an organic peroxy acid in the presence of a compound of a Group IV to Group VIII metal in the periodic table.

Step (b) has already been given adequate treatment above.

The partial reaction (a) may be illustrated diagramatically in the following manner:

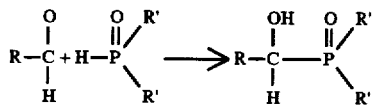

The statements made above with reference to the α-hydroxyalkyl phosphine oxides also apply to the substituents on the phosphorus atom and on the aldehyde as appropriate The disubstituted phosphine oxides are known in the art or can be prepared by conventional techniques (Houben-Weyl, *Methoden der organischen Chemie*, Vol. 12/1 (1963), pp. 193–199, 321; Vol. E1 (1982), pp. 240–245, 274). Of particular economical significance is the preparation of these compounds in situ from the corresponding disubstituted phosphine chlorides and at least a stoichiometric amount of water and preferably up to 2 mol of water per mole of phosphine chloride:

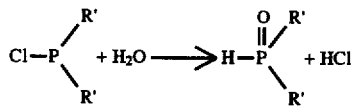

The acid liberated during the reaction can be neutralized by the addition of aqueous bases such as alkali metal carbonates, alkali metal bicarbonates, or alkali metal hydroxides, of which the sodium compounds are preferred. The neutralization is particularly simple to carry out when the reaction takes place in an inert organic solvent, since it is merely necessary to shake the organic phase with the aqueous base and then to continue with the reaction.

The disubstituted phosphine oxide and the aldehyde can be used in a molar ratio of from 0.5:1 to 1:1, but usually they are caused to react in stoichiometric amounts. It is particularly advantageous to carry out the reaction in the organic solvent in which the conversion of the chlorophosphine to the phosphine oxide took place, such as toluene, cyclohexane or petroleum ether. The process is usually carried out at room temperature, since reaction times of a few minutes to a few hours are generally satisfactory. It is, of course, alternatively possible to operate at an elevated temperature. To achieve simplicity of operation on an industrial scale the process is usually carried out under standard pressure conditions.

It has been found to be advantageous to carry out the reaction in the presence of a catalyst. This can be an alcoholate such as a methylate, ethylate, or isopropylate, the sodium alcoholates being preferred. Alkali metal fluorides such as sodium fluoride and potassium fluoride are also suitable compounds. These catalysts can be used in amounts of from 0.01 to 10 mol % and preferably from 0.1 to 1 mol % based on the aldehyde. The isolation of the compounds is carried out in known manner, preferably by crystallization.

A modification of the reaction described above comprises carrying out the hydrolysis of a disubstituted phosphine chloride in the presence of the aldehyde and causing the resulting reaction mixture to react immediately after it has been neutralized with an organic hydroperoxide or an organic peroxy acid in the presence of a compound of a Group IV to Group VIII metal as listed in the periodic table.

Novel α-hydroxybenzyl phosphine oxides of the general formula I

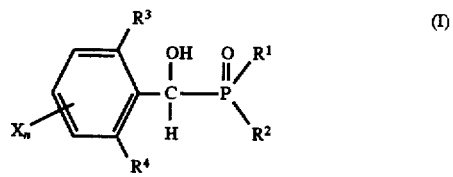

can be prepared by the partial process step (a) described above, in which the variables have the following meanings:

$R^1$, $R^2$ $C_1$–$C_{18}$ alkyl and preferably $C_6$–$C_8$ alkyl such as hexyl and octyl; $C_5$–$C_8$ cycloalkyl, such as cyclohexyl; $C_6$–$C_{12}$ aryl, such as especially phenyl, which can be monosubstituted or polysubstituted particularly by alkyl groups such as methyl, ethyl, isopropyl, alkoxy groups such as methoxy or ethoxy; $C_1$–$C_8$ alkoxy and preferably $C_1$–$C_4$ alkoxy such as methoxy, ethoxy, isopropoxy, n-butoxy;

$R^3$, $R^4$ $C_1$–$C_6$ alkyl and preferably methyl and ethyl; $C_1$–$C_6$ alkoxy and preferably methoxy and ethoxy; halogen and preferably chlorine and bromine;

X $C_1$–$C_6$ alkyl and preferably methyl; $C_1$–$C_6$ alkoxy and preferably methoxy; halogen and preferably chlorine; nitro; $C_1$–$C_4$ dialkylamino; cyano;

n 0 to 3 (where the substituents can be the same or different in the case of n>1) and preferably 0 or 1.

Preferred examples of the α-hydroxybenzyl phosphine oxides I of the invention are:

α-hydroxy-(2,6-dimethylbenzyl)-diphenyl phosphine oxide

α-hydroxy-(2,6-dichlorobenzyl)-diphenyl phosphine oxide

α-hydroxy-(2,6-dimethoxybenzyl)-diphenyl phosphine oxide

α-hydroxy-(2,4,6-trimethylbenzyl)-diphenyl phosphine oxide

α-hydroxy-(3-chloro-2,4,6-trimethylbenzyl)-diphenyl phosphine oxide

α-hydroxy-(2,6-dimethylbenzyl)-bis(2,5-dimethoxyphenyl) phosphine oxide

α-hydroxy-(2,6-dimethylbenzyl)-bis(4-methylphenyl) phosphine oxide

α-hydroxy-(2,4,6-trimethylbenzyl)-bis(2,5-dimethylphenyl) phosphine oxide

α-hydroxy-(2,4,6-trimethylbenzyl)-phenylethoxy phosphine oxide

The process of the invention allows for the preparation of α-hydroxyalkyl phosphine oxides and the sample oxidation thereof to the corresponding α-carbonylphosphine oxides. In addition, the particularly valuable α-hydroxyalkyl phosphine oxides carrying a 2,6-disubstituted phenyl group on the α-carbon atom can be prepared from readily available starting materials.

α-Carbonylphosphine oxides are used as photoinitiators in polymerizable compositions such as recording compositions or coating materials (EP-A 007,508).

EXAMPLES

1. Preparation of α-hydroxyalkyl phosphine oxides (process step (a))

Example 1

Preparation of α-hydroxy-(2,4,6-trimethylbenzyl)-diphenyl phosphine oxide (from chlorodiphenyl phosphine)

To a mixture of 9 g (0.5 mol) of water and 200 mL of toluene there were added 110 g (0.5 mol) of diphenyl chlorophosphine in 200 mL of toluene. The reaction mixture was extracted with 90 mL of 20 wt % strength caustic soda solution following a period of 1 h, and to the the organic phase of there were added 74 g (0.5 mol) of 2,4,6-trimethylbenzaldehyde and also 0.5 g of 30% strength sodium methylate solution in methanol. The product began to crystallize after 10 minutes, after which it was isolated in the usual manner. Yield 95%, top: 152°–153° C.

$^1$H-NMR (DMSO): 2.03 (br, 6 H); 2.16 (s, 3 H); 5.91 (dd, 1 H); 6.25 (dd, 1 H); 6.68 (s, 2 H); 7.38–7.88 (10 H) ppm
$^{31}$P-NMR (DMSO): 28.5 ppm

Example 2

Preparation of α-hydroxy-(2,4,6-trimethylbenzyl)-diphenyl phosphine oxide (from diphenyl phosphine oxide)

To 101 g (0.5 mol) of diphenyl phosphine oxide and 74 g (0.5 mol) of 2,4,6-trimethylbenzaldehyde in 150 mL of toluene there were added 0.5 g of a 30 wt % strength sodium methylate solution. The product began to crystallize after 10 minutes and was isolated in the usual manner. Yield: 98%.

Example 3

Preparation of α-hydroxy-(2,6-dichlorobenzyl)-diphenyl phosphine oxide 87.5 g (0.5 mol) of 2,6-dichlorobenzaldehyde were reacted in a manner similar to that described in Example 1.1. Yield: 96%, mp 205°–209° C.

$^1$H-NMR (DMSO): 6.37 (dd, 1 H); 6.67 (dd, 1 H); 7.22–7.93 (14 H) ppm
$^{31}$P-NMR (DMSO): 25.9 ppm 2. Preparation of α-carbonylphosphine oxides (process step b))

Example 4

Preparation of 2,4,6-trimethylbenzoyl diphenylphosphine oxide 31.5 g (0.1 mol) of α-hydroxy-(2,4,6-trimethylbenzyl)-diphenyl phosphine oxide and 0.9 g (3.4 mmol) of vanadyl (IV) bis-acetylacetonate in 150 g of chlorobenzene were admixed with 15 g (0.12 mol) of 70 wt % strength aqueous tert-butylhydroperoxide over a period of 30 minutes at 5° C. and stirred for 20 h at room temperature. The product was isolated by crystallization. Yield: 82%, mp 92°–94° C.

If 17.2 g (0.10 mol) of m-chloroperbenzoic acid are used instead of tert-butylhydroperoxide, the yield is 49%.

Example 5

Preparation of 2,6-dichlorobenzoyl diphenylphosphine oxide

To 15 g (0.04 mol) of α-hydroxy-(2,6-dichorobenzyl)-diphenyl phosphine oxide and 0.4 g (1.5 mmol) of vanadyl (IV) bis-acetylacetonate in 100 g of chlorobenzene there were added 12.9 g (0.1 mol) 70 wt % strength aqueous tert-butylhydroperoxide, and the mixture was kept at 70° C. for 5 h. The product was isolated by crystallization. Yield: 64%, mp 156°–158° C.

Example 6

Preparation of (3-chloro-2,4,6-trimethylbenzoyl) diphenylphosphine oxide

To 15.4 g (0.04 mol) of α-hydroxy-(3-chloro-2,4,6-trimethylbenzyl)-diphenyl phosphine oxide and 0.4 g (1.5 mmol) of vanadyl(IV) bis-acetylacetonate in 100 g of chlorobenzene there were added 8.2 g (0.06 mol) of 70 wt % strength aqueous tert-butylhydroperoxide and isolated by crystallization following a period of 20 h. Yield: 81%, mp 125°–126° C.

Example 7

Preparation of 2,4,6-trimethylbenzoyl phenylethoxyphosphine oxide

To 26.5 g (0.08 mol) of α-hydroxy-(2,4,6-trimethylbenzyl)-phenylethoxy phosphine oxide and 1 g (38 mmol) of vanadyl(IV) bis-acetylacetonate in 110 g of chlorobenzene there were added 28 g (0.22 mol) of 70 wt % strength aqueous tert-butylhydroperoxide and the mixture was stirred for a period of 20 h. The product was isolated by distillation. Yield: 55%, bp 180° C. (0.1 mbar).

Example 8

Preparation of diethyl butyrylphosphonate (butyryldiethoxy phosphine oxide)

To 16.2 g (77 mmol) of diethyl α-hydroxybutylphosphonate and 0.4 g (1.5 mmol) of vanadyl(IV) bis-acetylacetonate in 100 g of chlorobenzene there were added 30.4 g (0.24 mol) of 70 wt % strength aqueous tert-butylhydroperoxide and the mixture was stirred for 4 days. The solvent was removed in vacuo. Yield (in the residue): 25%

3. Preparation of α-caronyl phosphine oxides (process steps a) and b)).

Example 9

Preparation of 2,4,6-trimethylbenzoyldiphenyl phosphine oxide 550 g (2.5 mol) of diphenylchlorophosphine were added to 2.2 kg of chlorobenzene, 50 g of water and 370 g (2.5 mol) of 2,4,6-trimethylbenzaldehyde. The mixture was stirred at room temperature for 1 h, after which 500 g of 20% strength caustic soda solution were added.

Following the addition of 20 g (75 mmol) of vanadyl(IV) bis-acetylacetonate, 482 g (3.75 mol) of 70% strength aqueous tert-butylhydroperoxide were added to the reaction mixture at a temperature of from 5° to 10° C. After a period of 6 h, the pH was adjusted to 9 with 20% strength caustic soda solution and the phases were separated. The product was then isolated by crystallization. Yield: 85%.

We claim:

1. An α-hydroxybenzyl phosphine oxide of the general formula I

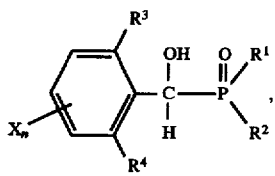

(I)

in which the variables have the following meanings:

$R^1$, $R^2$ $C_1$–$C_{18}$ alkyl, $C_5$–$C_8$ cycloalkyl, $C_6$–$C_{12}$ aryl, $C_1$–$C_8$ alkoxy;

$R^3$, $R^4$ $C_1$–$C_6$ alkyl, $C_1$–$C_6$ alkoxy;

X $C_1$–$C_6$ alkyl, $C_1$–$C_6$ alkoxy, halogen, nitro, $C_1$–$C_4$ dialkylamino, cyano;

n 0 to 3, and the substituents can be the same or different when n is greater than 1.

2. An α-hydroxybenzyl phosphine oxide as claimed in claim 1, wherein the variables have the following meanings:

$R^1$ $R^2$ phenyl, $C_1$–$C_8$ alkoxy;

$R^3$ $R^4$ methyl, methoxy;

X methyl;

n 1.

3. An α-hydroxybenzyl phosphine oxide as claimed in claim 1, wherein the variables have the following meanings:

$R^1$, $R^2$ phenyl or ethoxy;

$R^3$, $R^2$ methyl;

X methyl;

n 1.

* * * * *